US010905310B2

(12) United States Patent
Fujita

(10) Patent No.: US 10,905,310 B2
(45) Date of Patent: Feb. 2, 2021

(54) SIGNAL PROCESSING DEVICE AND MEDICAL OBSERVATION SYSTEM

(71) Applicant: SONY OLYMPUS MEDICAL SOLUTIONS INC., Tokyo (JP)

(72) Inventor: Noriaki Fujita, Tokyo (JP)

(73) Assignee: Sony Olympus Medical Solutions Inc., Tokyo (JP)

(*) Notice: Subject to any disclaimer, the term of this patent is extended or adjusted under 35 U.S.C. 154(b) by 0 days.

(21) Appl. No.: 16/377,021

(22) Filed: Apr. 5, 2019

(65) Prior Publication Data

US 2019/0223688 A1 Jul. 25, 2019

Related U.S. Application Data

(63) Continuation of application No. 15/558,592, filed as application No. PCT/JP2016/055097 on Feb. 22, 2016, now Pat. No. 10,292,569.

(51) Int. Cl.
*A61B 1/00* (2006.01)
*A61B 1/04* (2006.01)
(Continued)

(52) U.S. Cl.
CPC ............ *A61B 1/00006* (2013.01); *A61B 1/00* (2013.01); *A61B 1/00009* (2013.01);
(Continued)

(58) Field of Classification Search
CPC . A61B 1/00006; A61B 1/045; A61B 1/00009; A61B 1/06; A61B 1/00114; A61B 1/00045; A61B 1/04; A61B 1/00; G06T 7/0014; G06T 2207/10068; G06T 2200/28; H04N 7/10
(Continued)

(56) References Cited

U.S. PATENT DOCUMENTS 7,133,416 B1 * 11/2006 Chamdani .............. H04L 12/66 370/466
9,930,067 B1 3/2018 Johansson
(Continued)

FOREIGN PATENT DOCUMENTS

CN 101208037 A 6/2008
JP 2004-280605 A 10/2004
(Continued)

OTHER PUBLICATIONS

International Search Report dated May 24, 2016, in PCT/JP2016/055097, filed Feb. 22, 2016.
(Continued)

*Primary Examiner* — Jerome Grant, II
(74) *Attorney, Agent, or Firm* — Xsensus LLP

(57) ABSTRACT

A signal processing device is connected to an endoscope that examines a subject and outputs a signal in accordance with a result of the examination. The signal processing device includes a plurality of internal modules that process the signal output from the endoscope. The internal modules are connected via an interface supporting a communication protocol and having connector geometry, at least the communication protocol or both communication protocol and connector geometry conforming to a communication interface standard.

16 Claims, 7 Drawing Sheets

(51) Int. Cl.
*A61B 1/045* (2006.01)
*A61B 1/06* (2006.01)
*G06T 7/00* (2017.01)
*H04N 7/10* (2006.01)

(52) U.S. Cl.
CPC ...... *A61B 1/00045* (2013.01); *A61B 1/00114* (2013.01); *A61B 1/04* (2013.01); *A61B 1/045* (2013.01); *A61B 1/06* (2013.01); *G06T 7/0014* (2013.01); *G06T 2200/28* (2013.01); *G06T 2207/10068* (2013.01); *H04N 7/10* (2013.01)

(58) Field of Classification Search
USPC .......................................................... 382/128
See application file for complete search history.

(56) References Cited

U.S. PATENT DOCUMENTS

| | | | | |
|---|---|---|---|---|
| 10,032,003 | B2 | 7/2018 | Tong | |
| 10,459,870 | B2 * | 10/2019 | Joshua | H04L 67/12 |
| 2002/0080392 | A1 * | 6/2002 | Parvulescu | G06F 19/321<br>358/1.15 |
| 2003/0236446 | A1 * | 12/2003 | Eino | A61B 1/00105<br>600/160 |
| 2005/0283048 | A1 | 12/2005 | Gill et al. | |
| 2009/0062609 | A1 | 3/2009 | Suda | |
| 2009/0168835 | A1 * | 7/2009 | Heinke | G01J 5/02<br>374/121 |
| 2009/0218982 | A1 * | 9/2009 | Martin | H02J 7/35<br>320/101 |
| 2009/0292340 | A1 | 11/2009 | Mass | |
| 2011/0076983 | A1 | 3/2011 | Rofougaran | |
| 2011/0087756 | A1 | 4/2011 | Blondi et al. | |
| 2011/0212426 | A1 * | 9/2011 | Gloeggler | G09B 23/285<br>434/262 |
| 2012/0057615 | A1 * | 3/2012 | Weng | G01J 5/025<br>374/128 |
| 2012/0120217 | A1 | 5/2012 | Sasaki et al. | |
| 2013/0092173 | A1 * | 4/2013 | Alexander | A61B 1/00016<br>128/207.18 |
| 2014/0289434 | A1 * | 9/2014 | Ranganathan | G06F 13/42<br>710/105 |
| 2014/0337556 | A1 * | 11/2014 | Gu | G06F 1/1632<br>710/303 |
| 2015/0135209 | A1 * | 5/2015 | LaBosco | H04N 21/43635<br>725/31 |
| 2015/0149842 | A1 | 5/2015 | Yuan | |
| 2016/0296769 | A1 * | 10/2016 | Barthe | A61N 7/00 |
| 2017/0042631 | A1 | 2/2017 | Doo | |
| 2018/0028827 | A1 | 2/2018 | Schilling | |
| 2018/0070797 | A1 * | 3/2018 | Fujita | A61B 1/00 |

FOREIGN PATENT DOCUMENTS

| | | | |
|---|---|---|---|
| JP | 2007-50115 A | | 1/2007 |
| JP | 2007-50116 A | | 1/2007 |
| JP | 2007-50115 A | | 3/2007 |
| JP | 2007-50116 A | | 3/2007 |
| JP | 2008-513058 A | | 5/2008 |
| JP | 2009-50431 A | | 3/2009 |
| JP | 2009-195621 A | | 9/2009 |
| JP | 2010-4979 A | | 1/2010 |
| JP | 2012-105739 A | | 6/2012 |
| JP | 2013-39223 A | | 2/2013 |
| JP | 2014-36868 A | | 2/2014 |
| JP | 2014-210108 A | | 11/2014 |
| WO | WO 0177980 | | 10/2001 |
| WO | WO2007095499 | * | 8/2007 |

OTHER PUBLICATIONS

Office Action dated Nov. 26, 2018, in Chinese Patent Application No. 2016800234798 (with English-language translation), 14 pgs.
Japanese Office Action dated Sep. 3, 2019 in Japanese Application No. 2017-515404.
Japanese Office Action dated Jan. 21, 2020, issued in corresponding Japanese Patent Application No. 2017-515404.

* cited by examiner 1A
6A(60)
SIGNAL PROCESSING DEVICE
24A
CAMERA HEAD
3
61
FIRST INTERFACE MODULE
IF
62
CONTROL MODULE
IF
63
FIRST IMAGE PROCESSING MODULE
IF
61A
SECOND INTERFACE MODULE
IF
64
STORAGE MODULE
IF
63A
SECOND IMAGE PROCESSING MODULE
IF
IF
65
THIRD INTERFACE MODULE
5
4A
DISPLAY DEVICE 1B
6B
602B(602B2)
SECOND PROCESSING DEVICE
8
601B(601B1)
FIRST PROCESSING DEVICE
3
4
DISPLAY DEVICE
5
7
24
22
LIGHT SOURCE
2
23
21

1B
6B
SIGNAL PROCESSING DEVICE
601B(601B1)
FIRST PROCESSING DEVICE
24(2)
CAMERA HEAD
3
61
INTERFACE MODULE
5
4
DISPLAY DEVICE
8
602B(602B2)
SECOND PROCESSING DEVICE
62
CONTROL MODULE
IF
64
STORAGE MODULE
IF
63
IMAGE PROCESSING MODULE

SIGNAL PROCESSING DEVICE AND MEDICAL OBSERVATION SYSTEM

CROSS-REFERENCE TO RELATED APPLICATION

This application is a continuation application of and is based upon and claims the benefit of priority under 35 U.S.C. § 120 from U.S. application Ser. No. 15/558,592, filed Sep. 15, 2017, herein incorporated by reference, which is a National Stage Application of International Application No. PCT/JP2016/055097, filed Feb. 22, 2016, which claims the benefit of priority under 35 U.S.C. § 119 from Japanese Patent Application No. 2015-093673, filed Apr. 30, 2015.

FIELD

The present invention relates to a signal processing device that processes a signal output from a medical observation apparatus such as an endoscope, and a medical observation system including the signal processing device.

BACKGROUND

In the medical field, medical observation systems that capture, for example, a subject inside a living body with an imaging device to observe the subject have been known (see Patent Literature 1, for example).

The medical observation system (rigid endoscope system) disclosed in Patent Literature 1 includes an endoscope (rigid endoscope imaging apparatus) that captures an image inside a living body, a signal processing device (processor) that processes an imaging signal from the endoscope, and a display device (monitor) that displays a captured image based on a video signal processed by the signal processing device.

The signal processing device includes a plurality of internal modules such as a central processing unit (CPU), image input controllers, an image processing unit, and a video output unit that are connected via certain interfaces so that the internal modules can transmit and receive information to and from one another.

CITATION LIST

Patent Literature

Patent Literature 1: Japanese Patent Application Laid-open No. 2013-039223

SUMMARY

Technical Problem

Many conventional medical observation systems use dedicated interfaces produced by the medical observation system manufacturers, not using interfaces conforming to a communication interface standard (standard communication protocol), as the interfaces that connect a plurality of internal modules.

Using the dedicated interfaces requires the medical observation system manufacturers to newly develop the dedicated interfaces upon modification of the internal modules to adjust to, for example, a highly pixelated endoscope (imaging device). Thus, there has been a problem in that it takes a longer development period to develop a new model, thereby requiring a larger development cost.

The present invention has been made in view of the foregoing, and it is an object of the present invention to provide a signal processing device and a medical observation system that require a shorter development period in a new model development and thus can reduce the development cost.

Solution to Problem

To solve the above described problem and achieve the object, a signal processing device according to the present invention is a signal processing device that is connected to a medical observation apparatus that performs examination on a subject and outputs a signal in accordance with a result of the examination, and includes: a plurality of internal modules configured to process the signal output from the medical observation apparatus, wherein the internal modules are connected via an interface supporting a communication protocol and having a connector geometry, at least the communication protocol or both communication protocol and connector geometry conforming to a communication interface standard.

In the above-described signal processing device according to the present invention, any one of the internal modules is a control module including a main board on which a central processing unit is installed.

In the above-described signal processing device according to the present invention, any one of the internal modules is an image processing module configured to perform image processing.

In the above-described signal processing device according to the present invention, any one of the internal modules is a storage module configured to store therein a computer program for causing the image processing module to perform the image processing.

In the above-described signal processing device according to the present invention, any one of the internal modules is a relay module configured to convert the signal output from the medical observation apparatus into a signal conforming to the communication interface standard and output the converted signal to another internal module.

In the above-described signal processing device according to the present invention, any one of the internal modules is an image processing module configured to perform image processing, and the relay module is configured to perform image processing on behalf of the image processing module when a failure occurs in the image processing module.

In the above-described signal processing device according to the present invention, the image processing module is configured to perform the image processing by software processing, and the relay module is configured to perform the image processing by using a hardware configuration.

In the above-described signal processing device according to the present invention, any one of the internal modules is an image processing module configured to perform image processing, the internal modules are divided into a first group including the relay module and a second group including the image processing module, and the signal processing device includes a first outer housing configured to store therein the internal module of the first group, and a second outer housing that is configured separately from the first outer housing and that stores therein the internal module of the second group.

A medical observation system according to the present invention includes a medical observation apparatus configured to perform an examination on a subject and outputs a signal in accordance with a result of the examination; and the above-described signal processing device.

In the above-described medical observation system according to the present invention, the medical observation apparatus includes an imaging unit that captures an image of the subject and outputs an imaging signal obtained by capturing the image as the signal output in accordance with the result of the examination.

Advantageous Effects of Invention

In the signal processing device according to the present invention, a plurality of internal modules are connected via an interface supporting a communication protocol and having a connector geometry, at least the communication protocol or both communication protocol and connector geometry conforming to a communication interface standard (e.g., PC/AT-compatibles standard). In other words, the signal processing device according to the present invention is constructed using a general-purpose computer architecture.

When at least one of the internal modules needs to be modified to adjust to the specification change in a medical observation apparatus, for example, this eliminates the need for the conventional efforts to newly develop the dedicated interface, and allows the internal module to be modified by using, for example, a general-purpose PC part conforming to a communication interface standard (e.g., PC/AT-compatibles standard) to adjust to the specification change in the medical observation apparatus. Thus, the signal processing device according to the present invention exhibits effects, for example, that the signal processing device can be developed in a shorter development period and with a reduced development cost in the development of its new model.

The medical observation system according to the present invention includes the signal processing device described above, and thus has the same effects as the signal processing device.

DESCRIPTION OF EMBODIMENTS

The following describes embodiments of the present invention (hereinafter, embodiments) with reference to the accompanying drawings. The embodiments described below are not intended to limit the scope of the present invention. The accompanying drawings include like reference signs referring to like parts.

First Embodiment

General Configuration of Medical Observation System

Figure 1:
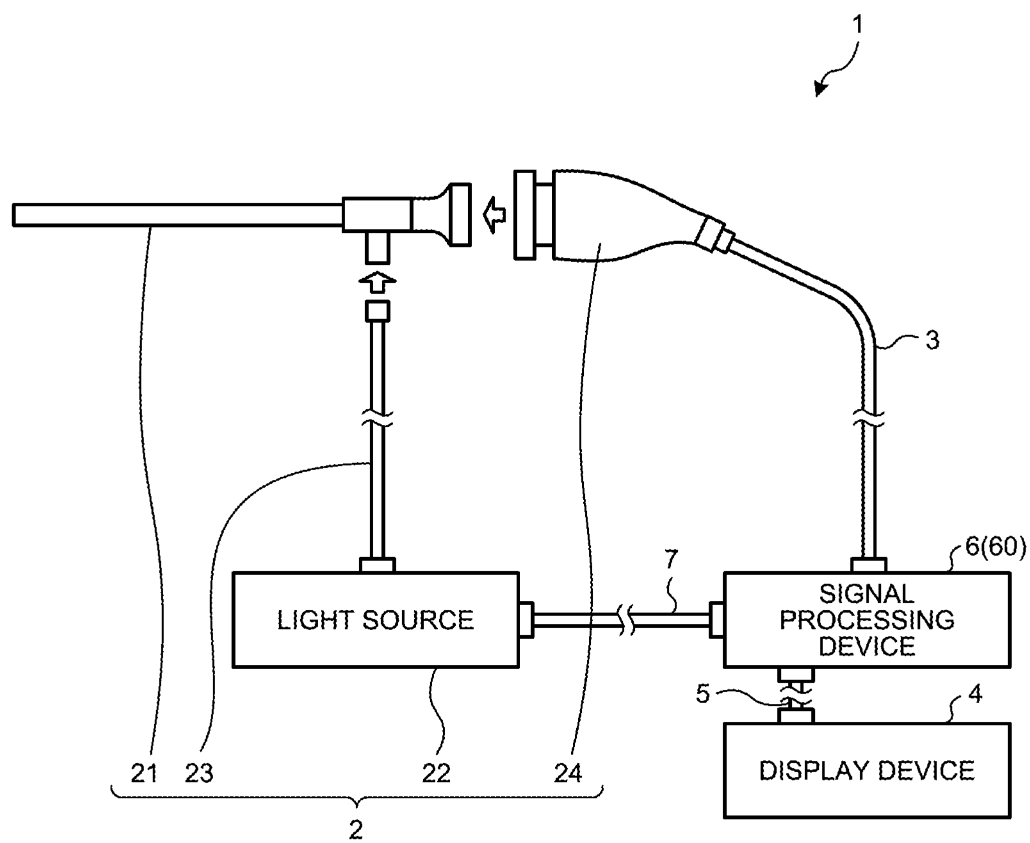
FIG. 1 is a diagram illustrating a general configuration of a medical observation system according to a first embodiment of the present invention.

FIG. 1 is a diagram illustrating a general configuration of a medical observation system 1 according to a first embodiment of the present invention.

The medical observation system 1 is a system for use in the medical field for observing a subject inside a living body, for example. As illustrated in FIG. 1, the medical observation system 1 includes an endoscope 2, a first transmission cable 3, a display device 4, a second transmission cable 5, a signal processing device 6, and a third transmission cable 7.

The endoscope 2 functions as a medical observation apparatus according to the present invention, and is used to examine the inside of a living body and outputs a signal in accordance with the result of the examination. As illustrated in FIG. 1, the endoscope 2 includes an insert 21, a light source 22, a light guide 23, and a camera head 24.

The insert 21 has a rigid elongated shape and is inserted into the living body. The insert 21 includes an optical system including one or more lenses for collecting a subject image.

The light source 22 is connected with an end of the light guide 23 and provides light to the end of the light guide 23 under the control of the signal processing device 6 to illuminate the inside of the living body.

The end of the light guide 23 is detachably connected to the light source 22 and the other end thereof is detachably connected to the insert 21. The light guide 23 transmits the light provided by the light source 22 from the end to the other end to provide the light to the insert 21. The light provided to the insert 21 is emitted from a leading end of the insert 21 to illuminate the inside of the living body. The light (subject image) illuminating the inside of the living body is collected by the optical system in the insert 21.

The camera head 24 is detachably connected to a base end of the insert 21. The camera head 24 functions as an imaging unit according to the present invention, and captures the subject image collected by the insert 21 and outputs an imaging signal (corresponding to a signal in accordance with a result of the examination according to the present invention) obtained by capturing the image under the control of the signal processing device 6.

In the first embodiment, the camera head 24 includes a single imaging device (not illustrated) that generates the imaging signal. The camera head 24 photoelectrically converts the imaging signal into an optical signal, and outputs the imaging signal in the form of the optical signal.

An end of the first transmission cable 3 is detachably connected to the signal processing device 6, and the other end thereof is detachably connected to the camera head 24. Specifically, the first transmission cable 3 includes a plurality of electric wires (not illustrated) and an optical fiber (not illustrated) inside a coat that is the outermost layer of the first transmission cable 3.

The electric wires are electric wires for individually transmitting, for example, a control signal, a synchronization signal, a clock, and electric power output from the signal processing device 6 to the camera head 24.

The optical fiber is an optical fiber for transmitting the imaging signal (optical signal) output from the camera head 24 to the signal processing device 6.

When the camera head 24 is configured to output the imaging signal in the form of an electric signal, the optical fiber may be changed to an electric wire. When the signal processing device 6 is configured to output at least one of the signals such as the control signal, synchronization signal, and clock in the form of an optical signal, the electric wire for use in transmitting the signal may be changed to an optical fiber.

The display device 4, which is, for example, a monitor from standard definition (SD), high definition (HD), to 4K and beyond, displays an image under the control of the signal processing device 6.

An end of the second transmission cable 5, which is, for example, a high definition serial digital interface (HD-SDI) or a 3G-SDI cable, a high-definition multimedia interface (HDMI, registered trademark) cable or a DisplayPort (registered trademark) cable, is detachably connected to the display device 4 and the other end thereof is detachably connected to the signal processing device 6. The second transmission cable 5 transmits a video signal processed at the signal processing device 6 to the display device 4.

The signal processing device 6 includes a CPU and other components, and centrally controls the operations of the light source 22, the camera head 24, and the display device 4.

An end of the third transmission cable 7 is detachably connected to the light source 22, and the other end thereof is detachably connected to the signal processing device 6. The third transmission cable 7 transmits a control signal from the signal processing device 6 to the light source 22.

Configuration of Signal Processing Device

Described next is a configuration of the signal processing device 6.

The following mainly describes the signal processing device 6 with respect to its function of processing the imaging signal received from the camera head 24 via the first transmission cable 3.

Figure 2:
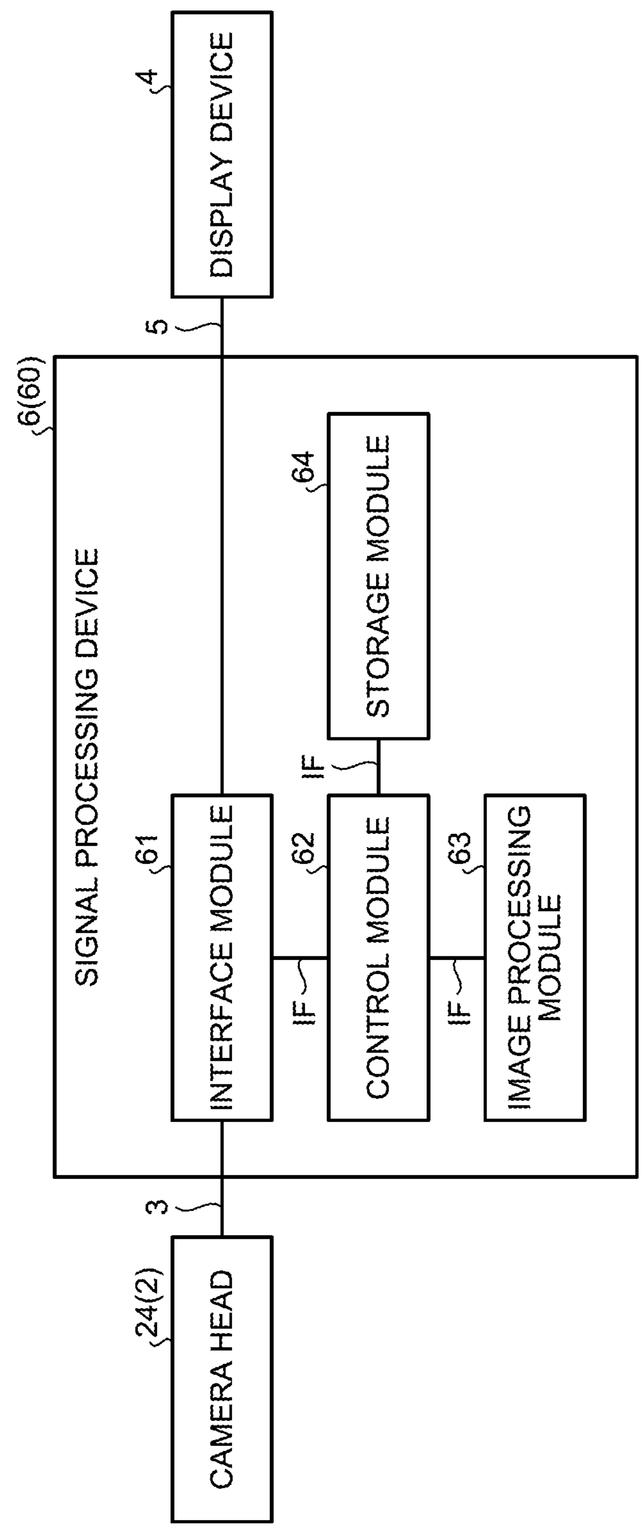
FIG. 2 is a block diagram illustrating a configuration of a signal processing device illustrated in FIG. 1.

FIG. 2 is a block diagram illustrating a configuration of the signal processing device 6.

FIG. 2 eliminates the illustration of a connector that detachably connects the camera head 24 and the first transmission cable 3, a connector that detachably connects the first transmission cable 3 and the signal processing device 6, a connector that detachably connects the display device 4 and the second transmission cable 5, and a connector that detachably connects the second transmission cable 5 and the signal processing device 6. FIG. 2 illustrates the electric wires and the optical fiber constituting the first transmission cable 3 as one cable.

The signal processing device 6 is constructed using the general-purpose computer architecture.

Specifically, as illustrated in FIG. 2, the signal processing device 6 includes an interface module 61, a control module 62, an image processing module 63, and a storage module 64 that are connected via general-purpose interfaces IF, and these modules function as a plurality of internal modules according to the present invention.

The signal processing device 6 (the internal modules 61 to 64) is disposed inside a single outer housing 60 (FIG. 1). The signal processing device 6 after having being assembled, tested, and through other procedures is unopenably set inside the outer housing 60.

The internal modules 61 to 64 may be configured as a plurality of separate modules one of which includes at least one internal module separated from the other internal modules, and any two or three of the internal modules 61 to 64 may be combined as one module.

Each interface IF supports a communication protocol and has a connector geometry, at least the communication protocol or both communication protocol and connector geometry conforming to a communication interface standard (e.g., PC/AT-compatibles standard).

In the first embodiment, the signal processing device 6 includes, for example, peripheral component interconnect express (PCIe, registered trademark) interfaces as the interfaces IF. In the first embodiment, the internal modules 62 to 64 each include what is called a PC part conforming to the PCIe standard. In other words, the interface module 61 has connection units other than the interface IF. However, the interface module 61 may include what is called a PC part in the same manner as the other internal modules 62 to 64.

The control module 62 controls the operation of the light source 22, the operation of the camera head 24, the operation of the display device 4, and the entire operation of the signal processing device 6.

In the first embodiment, the control module 62 includes a motherboard (main board) on which a CPU and other components are installed and that conforms to the PC/AT-compatibles standard. The motherboard is provided with expansion slots (PCIe slots in the first embodiment) to which the interface module 61, the image processing module 63, and the storage module 64 are connected.

At least one of the interfaces IF connecting the internal modules 61 to 64 may have a connector geometry not conforming to the communication interface standard and may have, for example, an original connector geometry. Moreover, the at least one of the interfaces IF may be an interface IF that directly connects the internal modules by, for example, electric wiring without using connectors and that supports the communication protocol of the communication interface standard.

The interface module 61 functions as a relay module according to the present invention, and is mounted to an expansion slot (a PCIe slot in the first embodiment) provided in the control module 62.

Figure 7:
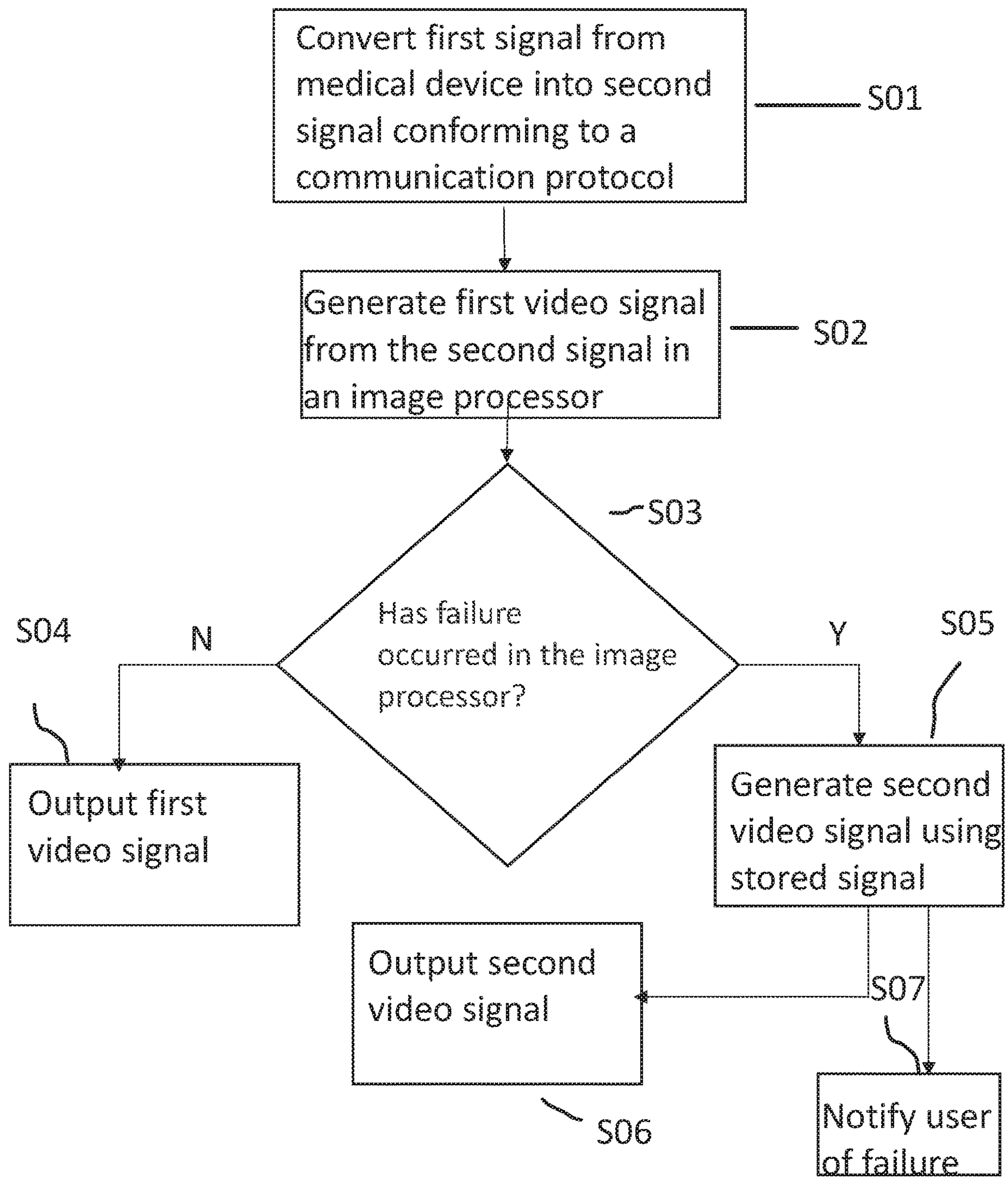
FIG. 7 is a diagram illustrating a flowchart according to an embodiment of the present invention.

Specifically, as shown in operation S01 of FIG. 7, the interface module 61 photoelectrically converts an imaging signal (optical signal) received from the camera head 24 via the first transmission cable 3 into an electric signal, and converts the photoelectrically converted imaging signal into a digital signal conforming to a communication interface standard (PCIe standard in the first embodiment). The interface module 61 temporarily stores the converted digital signal in a memory (not illustrated) such as a video random access memory (VRAM) and then outputs the digital signal to the control module 62 via the interface IF.

The interface module 61 receives, from the control module 62, a first video signal generated by the image processing module 63, as shown in operation S02 of FIG. 7, via the interface IF and outputs the first video signal to the display device 4 via the second transmission cable 5, as shown in operation S04 of FIG. 7. Upon receiving the first video signal, the display device 4 displays an image (hereinafter referred to as an ordinary image) based on the first video signal.

If, for example, a failure occurs in the image processing module 63, determined in operation S03 of FIG. 7, the interface module 61 performs various types of image processing (simplified image processing compared to the processing performed by the image processing module 63, that is, image processing that requires a lower processing load) on the signal stored in the memory (not illustrated) such as the VRAM on behalf of the image processing module 63, and generates a second video signal as shown in operation S05 of FIG. 7. The interface module 61 then outputs the second video signal to the display device 4 via the second transmission cable 5, as shown in operation S06 of FIG. 7. Upon receiving the second video signal, the display device 4 displays an image (hereinafter referred to as a simplified image) based on the second video signal.

It is preferred that the interface module 61 performs the image processing by using a hardware configuration, not by software processing. In other words, it is preferred that the image processing function of the interface module 61 is implemented by a hardware configuration such as a programmable logic device.

The interface module 61 may implement the image processing function on behalf of the image processing module 63 only when a failure occurs in the image processing module 63. The image processing function is performed by the interface module 61, but is not limiting as described above. The image processing function may be performed by a configuration provided separately from the interface module 61.

The failure occurring in the image processing module 63 can be detected, for example, from frame IDs given to the first video signal as described below.

In other words, the camera head 24 outputs an imaging signal (optical signal) including frame IDs (hereinafter referred to as first frame IDs) given to frames in chronologically sequential order to the signal processing device 6 via the first transmission cable 3. The control module 62 copies the first frame IDs given by the camera head 24 to the frames, and gives new frame IDs (hereinafter referred to as second frame IDs) to the frames in the first video signal generated by the image processing module 63.

The interface module 61 checks, for example, the first frame IDs included in the received imaging signal and the second frame IDs included in the first video signal, and determines whether the first frame ID matches the second frame ID in each frame and/or whether the first frame IDs (the second frame IDs as well) are given to the frames in sequential order, as shown in operation S03 in FIG. 7. When the first frame ID matches the second frame ID in each frame and/or the first frame IDs (the second frame IDs as well) are given to the frames in sequential order, the interface module 61 determines that no failure is occurring in the image processing module 63 (that the image processing module 63 is in a normal state), as shown in operation S04 in FIG. 7, such that the first video signal is output. On the other hand, when the first frame ID does not match the second frame ID in each frame and/or the first frame IDs (the second frame IDs as well) are not given to the frames in sequential order, the interface module 61 determines that a failure has occurred in the image processing module 63 (that an abnormality has occurred in the image processing module 63), as shown in operation SOS in FIG. 7, such that the second video signal is output.

The signal processing device 6 includes a notification unit (not illustrated) for notifying a user that a failure has occurred in the image processing module 63. The notification unit notifies the user of the occurrence of a failure by displaying this information on a display unit (not illustrated) of the signal processing device 6 or on the display device 4, or by outputting sound, as shown in operation S07 of FIG. 7.

For example, at least one function of the interface module 61 may be separated from the other functions thereof and the interface module 61 may include a plurality of modules corresponding to the separated functions. The function of generating the second video signal may be separated from the other functions of the interface module 61, and the interface module 61 may include modules corresponding to the separated functions. For example, the function of converting an imaging signal received from the imaging device (not illustrated) of the camera head 24 into a digital signal conforming to a communication protocol of a communication interface standard may be separated from the other functions of the interface module 61, and the interface module 61 may include modules corresponding to the separated functions. Furthermore, the function of converting the imaging signal into the digital signal may be included in the camera head 24 or the first transmission cable 3 outside of the signal processing device 6.

The image processing module 63 includes, for example, a general-purpose computing on graphics processing unit (GPGPU) and is mounted to an expansion slot (a PCIe slot in the first embodiment) provided in the control module 62.

Specifically, the image processing module 63 performs various types of image processing such as development, noise reduction, color correction, color enhancement, and edge enhancement on the digital signal (imaging signal) output from the interface module 61 and received via the interfaces IF and the control module 62, and generates a first video signal. The image processing module 63 outputs the first video signal to the control module 62 via the interface IF. It is preferred that the image processing module 63 performs the image processing by software processing.

The storage module 64 includes, for example, a solid state drive (SSD), a hard disk drive (HDD), or a dual inline memory module (DIMM), and is mounted to an expansion slot, which is an integrated drive electronics (IDE) or a serial advanced technology attachment (SATA) connector and memory socket in the first embodiment, provided in the control module 62.

Specifically, the storage module 64 stores therein computer programs for causing the image processing module 63 to perform various types of image processing, and an operating system (OS) such as Windows (registered trademark), Linux (registered trademark), Android (registered trademark), iOS (registered trademark) or a real-time operating system (RTOS).

In the signal processing device 6 according to the first embodiment, the internal modules 61 to 64 are connected via interfaces IF (e.g., PCIe interfaces in the first embodiment) supporting a communication protocol and having a connector geometry, at least the communication protocol or both communication protocol and connector geometry conforming to a communication interface standard (e.g., PC/AT-compatibles standard). In other words, the signal processing device 6 is constructed using a general-purpose computer architecture.

For example, using the general-purpose computer architecture eliminates the need for the conventional efforts to newly develop the dedicated interface when at least one of the internal modules 61 to 64 needs to be modified in accordance with the specification change (e.g., a highly pixelated camera head 24) in the endoscope 2. The internal module can be modified by using, for example, a general-purpose PC part (e.g., the control module 62 including a motherboard on which a CPU is installed, the image processing module 63 such as a GPGPU, and the storage module 64 such as an SSD) conforming to a communication interface standard (e.g., PC/AT-compatibles standard) to adjust to the specification change in the endoscope 2. The first embodiment exhibits an effect that the signal processing device 6 can be developed in a shorter development period and with a reduced development cost in the development of a new model of the signal processing device 6, for example.

Rapid advances in technology increase the processing speed of the general-purpose PC parts such as a GPGPU that performs image processing, and increase the storage capacity of the general-purpose PC parts such as an SSD that stores data. It is preferred, therefore, that the latest high-speed, high-capacity general-purpose PC parts are used for the image processing module 63 and/or the storage module 64 in the development of a new model of the signal processing device 6. In this case, it is preferred that, for example, the image processing module 63 and the control module 62 and/or the storage module 64 and the control module 62 are connected via an interface IF supporting a communication protocol and having a connector geometry that conform to a communication interface standard.

The interface module 61 differs from the control module 62, the image processing module 63, and the storage module 64 in that the interface module 61 is a dedicated module to a certain model of the endoscope 2 (camera head 24), whereas the control module 62, the image processing module 63, and the storage module 64 are general-purpose PC parts.

However, the interface module 61 also uses the interface IF that conforms to the communication interface standard (e.g., PC/AT-compatibles standard). Determining to use an interface IF conforming to the communication interface standard (e.g., PC/AT-compatibles standard) for, for example, a newly developed dedicated module for a new endoscope 2 (camera head 24) allows the internal modules 62 to 64 in the existing signal processing device 6 to be used for the new endoscope 2. This configuration can prevent an increase in the development period and the development cost for the development of a new model of the signal processing device 6.

The signal processing device 6 according to the first embodiment includes the storage module 64 that stores therein computer programs for causing the image processing module 63 to perform various types of image processing, and an OS such as Windows (registered trademark), Linux (registered trademark), Android (registered trademark), iOS (registered trademark), or an RTOS.

Changing, as appropriate, the computer programs stored in the storage module 64 can eliminate the need for changing the hardware configuration in the development of a new model.

The signal processing device 6 according to the first embodiment is configured such that the interface module 61 performs image processing on behalf of the image processing module 63 when a failure occurs in the image processing module 63.

The interface module 61 proactively outputs the second video signal when a failure occurs in the image processing module 63, and thus, a simplified image based on the second video signal can be displayed, although the simplified image has a lower image quality than that of the ordinary image based on the first video signal. This configuration can prevent a captured image based on an imaging signal from the camera head 24 from disappearing in the middle of the process when a failure occurs in the image processing module 63.

In particular, implementing the image processing function of the interface module 61 by a hardware configuration such as a programmable logic device can reduce the probability of failure compared to the image processing module 63 that performs software processing. This configuration has a favorable effect of preventing an image from disappearing.

Second Embodiment

Described next is a second embodiment of the present invention.

In the following description, the same reference signs refer to the same configurations as those in the first embodiment, and detailed description thereof is omitted or simplified.

In the medical observation system 1 according to the first embodiment, the camera head 24 includes a single imaging device.

A medical observation system according to the second embodiment includes, for example, an operating microscope, and can display, for example, a subject inside a living body or a subject on a surface of a living body as a magnified three-dimensional image. In the medical observation system according to the second embodiment, the camera head includes two imaging devices that generate two imaging signals with parallax, for example.

The following describes a configuration of a signal processing device included in the medical observation system according to the second embodiment.

Configuration of Signal Processing Device

Figure 3:
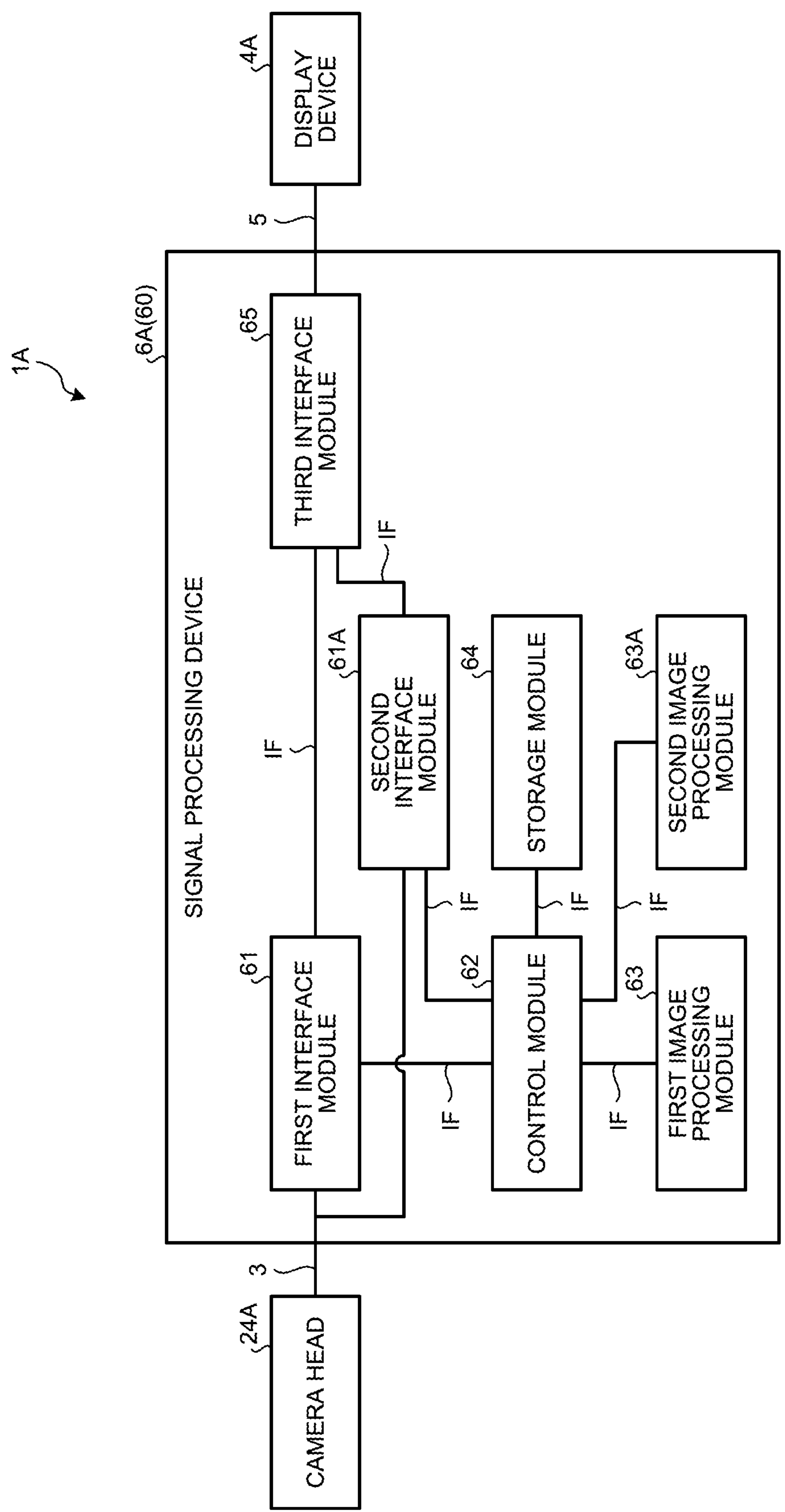
FIG. 3 is a block diagram illustrating a configuration of a signal processing device according to a second embodiment of the present invention.

FIG. 3 is a block diagram illustrating a configuration of a signal processing device 6A according to the second embodiment of the present invention.

FIG. 3 eliminates the illustration of a connector that detachably connects a camera head 24A and the first transmission cable 3, a connector that detachably connects the first transmission cable 3 and the signal processing device 6A, a connector that detachably connects a display device 4A and the second transmission cable 5, and a connector that detachably connects the second transmission cable 5 and the signal processing device 6A in the same manner as in FIG. 2.

As illustrated in FIG. 3, the signal processing device 6A included in a medical observation system 1A according to the second embodiment additionally includes a second interface module 61A, a second image processing module 63A, and a third interface module 65 that are internal modules mounted to expansion slots (PCIe slots, for example) provided in the control module 62, as compared to the signal processing device 6 (FIG. 2) described in the first embodiment above.

In the following description, the interface module 61 and the image processing module 63 described in the first embodiment above are referred to as a first interface module 61 and a first image processing module 63, respectively, in order to distinguish these modules from the second interface module 61A and the second image processing module 63A.

The camera head 24A (FIG. 3) according to the second embodiment is provided with two imaging devices (another imaging device is added to the camera head 24 described in the first embodiment above), and thus the second interface module 61A is additionally included. The second interface module 61A has the same function as the first interface module 61.

In other words, the first interface module 61 performs processing on an imaging signal generated by one of the two imaging devices. The second interface module 61A performs processing on an imaging signal generated by the other imaging device.

In the second embodiment, as illustrated in FIG. 3, the first interface module 61 outputs the first video signal and the second video signal to the third interface module 65 via the interface IF, not to the display device 4A. The second interface module 61A outputs the video signals in the same manner as the first interface module 61.

The camera head 24A is provided with the two imaging devices, and thus the second image processing module 63A is additionally included. The second image processing module 63A has the same function as the first image processing module 63.

That is, the first image processing module 63A performs processing on a digital signal (imaging signal) generated by one of the two imaging devices and received from the first interface module 61 via the interfaces IF and the control module 62. Meanwhile, the second image processing module 63A performs processing on a digital signal (imaging signal) generated by the other imaging device and received from the second interface module 61A via the interfaces IF and the control module 62.

The third interface module 65, upon receiving the first video signals from the first and the second interface modules 61 and 61A via the interfaces IF, performs certain signal processing on the first video signals to generate a first three-dimensional video signal for displaying a three-dimensional image. The third interface module 65, upon receiving the second video signals from the first and the second interface modules 61 and 61A via the interfaces IF, performs certain signal processing on the second video signals to generate a second three-dimensional video signal for displaying a three-dimensional image.

The third interface module 65 outputs the generated first or second three-dimensional video signal to the display device 4A via the second transmission cable 5.

When, for example, a failure occurs in at least one of the first and the second image processing modules 63 and 63A, the third interface module 65 may output a first or a second two-dimensional video signal for displaying a two-dimensional image to the display device 4A by using any one of the video signals received by the third interface module 65 that are the first video signal from the other one of the first and the second image processing modules 63 and 63A having no failure and the second video signals from the first and the second interface modules 61 and 61A.

This configuration can prevent a captured image based on an imaging signal from the camera head 24A from disappearing in the middle of the process when a failure occurs in at least one of the first and the second image processing modules 63 and 63A.

The display device 4A includes, for example, a three-dimensional (3D) display such as an integral imaging 3D display or a multiview display. The display device 4A displays a three-dimensional image based on the first or the second three-dimensional video signal received via the second transmission cable 5.

The third interface module 65 provides a synchronization signal and a clock to the two imaging devices in the camera head 24A via the interfaces IF, the first and the second interface modules 61 and 61A, and the first transmission cable 3 in order to synchronize the imaging devices.

The medical observation system 1A configured in accordance with the second embodiment above has the same effect as in the first embodiment.

Third Embodiment

Described next is a third embodiment of the present invention.

In the following description, the same reference signs refer to the same configurations as those in the first embodiment, and detailed description thereof is omitted or simplified.

In the medical observation system 1 according to the first embodiment above, the signal processing device 6 (internal modules 61 to 64) are disposed inside the single outer housing 60.

In the medical observation system according to the third embodiment, the signal processing device 6 (internal modules 61 to 64) is divided into two groups, and the two groups are separately disposed in different outer housings.

The following describes a configuration of a signal processing device included in the medical observation system according to the second embodiment.

Configuration of Signal Processing Device

Figure 4:
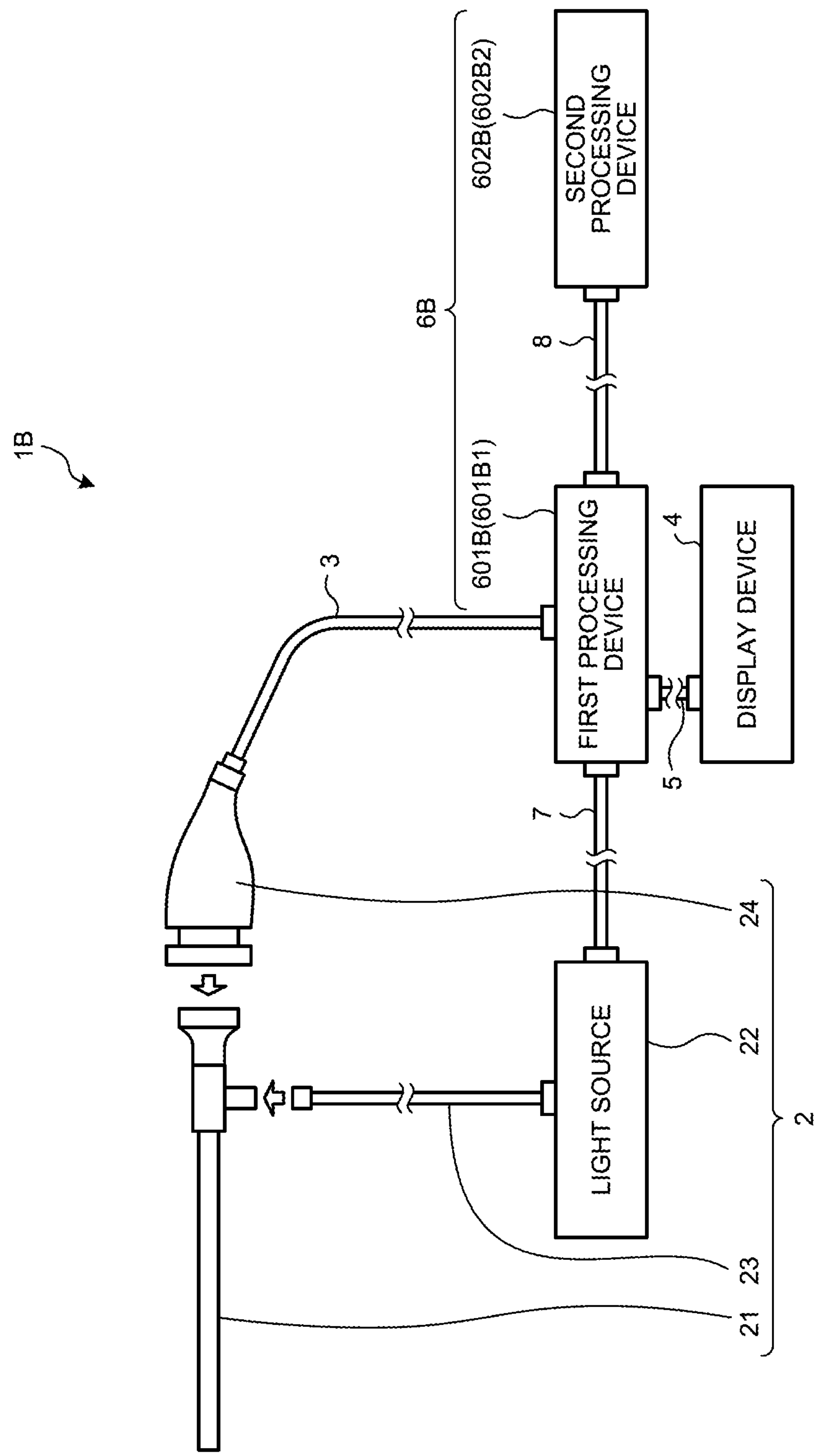
FIG. 4 is a diagram illustrating a general configuration of a signal processing device according to a third embodiment of the present invention.
Figure 5:
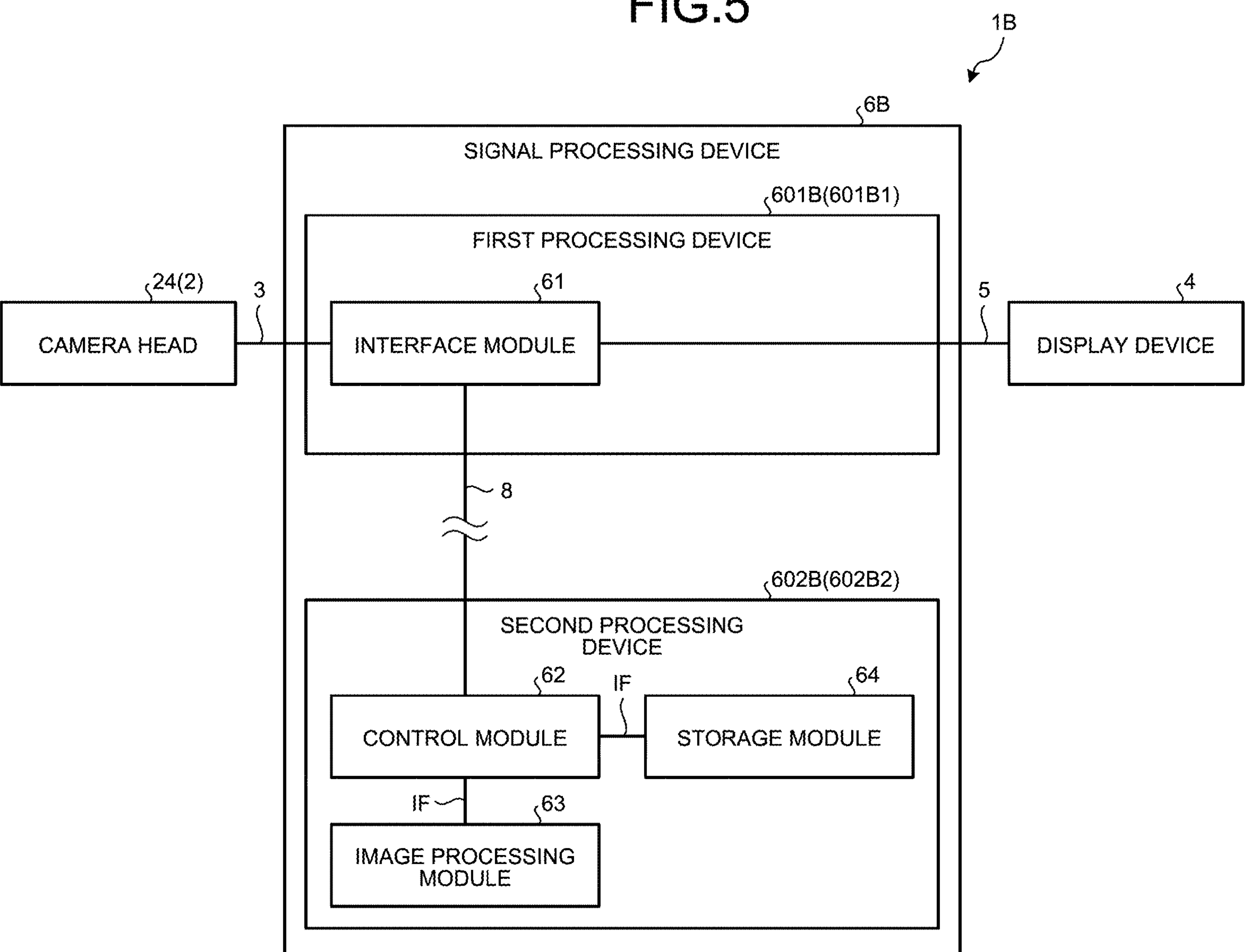
FIG. 5 is a block diagram illustrating a configuration of the signal processing device illustrated in FIG. 4.

FIG. 4 is a diagram illustrating a general configuration of a signal processing device 6B according to the third embodiment of the present invention. FIG. 5 is a block diagram illustrating a configuration of the signal processing device 6B illustrated in FIG. 4.

Specifically, as illustrated in FIG. 4, the signal processing device 6B included in a medical observation system 1B according to the third embodiment is divided into a first processing device 601B and a second processing device 602B, and these processing devices 601B and 602B are connected via a fourth transmission cable 8.

As illustrated in FIG. 5, the first processing device 601B includes the interface module 61 that is disposed inside a first outer housing 601B1.

The first processing device 601B (interface module 61) is connected to the camera head 24 via the first transmission cable 3, and is connected to the display device 4 via the second transmission cable 5 in the same manner as in the first embodiment above.

As illustrated in FIG. 5, the second processing device 602B includes the control module 62, the image processing module 63, and the storage module 64 that are disposed inside a second outer housing 602B2.

The fourth transmission cable 8 conforms to a communication interface standard (e.g., PC/AT-compatibles standard). An end of the fourth transmission cable 8 is detachably connected to the first processing device 601B and the other end thereof is detachably connected to the second processing device 602B. Through the fourth transmission cable 8, signals are transmitted and received between the interface module 61 and the control module 62 in the same manner as in the first embodiment above.

In the third embodiment, the first and the second processing devices 601B and 602B are connected via a wire (the fourth transmission cable 8), but are not limited to this. The first and the second processing devices 601B and 602B may be connected wirelessly.

The signal processing device 6B according to the third embodiment is configured to allow the interface module 61 to perform image processing on behalf of the image processing module 63 and output a second video signal to the display device 4 when a failure occurs not only in the image processing module 63 but also, for example, in the second processing device 602B itself or the fourth transmission cable 8.

With this configuration, the interface module 61 proactively outputs the second video signal when a failure occurs in the second processing device 602B itself or the fourth transmission cable 8, and thus, a simplified image based on the second video signal can be displayed, although the simplified image has a lower image quality than that of the ordinary image based on the first video signal. This configuration can prevent a captured image based on an imaging signal from the camera head 24 from disappearing in the middle of the process even when a failure occurs in the second processing device 602B itself or the fourth transmission cable 8.

According to the third embodiment described above, the following effects can be obtained in addition to the same effects as those described in the first embodiment above.

The signal processing device 6B according to the third embodiment is divided into the first processing device 601B and the second processing device 602B, and these processing devices 601B and 602B are connected via the fourth transmission cable 8 (hereinafter referred to as separate configuration).

With this configuration, for example, the first processing device 601B can be placed inside an operating room, and the second processing device 602B can be placed in a location other than the operating room. In other words, disposing the internal modules 61 to 64 in a single outer housing (hereinafter referred to as an integral configuration) limits the options of the internal modules 62 to 64 that are general-purpose PC parts in terms of power to be consumed, heat to be generated, and physical dimensions thereof, for example. The separate configuration according to the third embodiment can avoid such limitation, and thus, high-performance PC parts can be selected as the internal modules 62 to 64.

Fourth Embodiment

Described next is a fourth embodiment of the present invention.

In the following description, the same reference signs refer to the same configurations as those in the third embodiment, and detailed description thereof is omitted or simplified.

Figure 6:
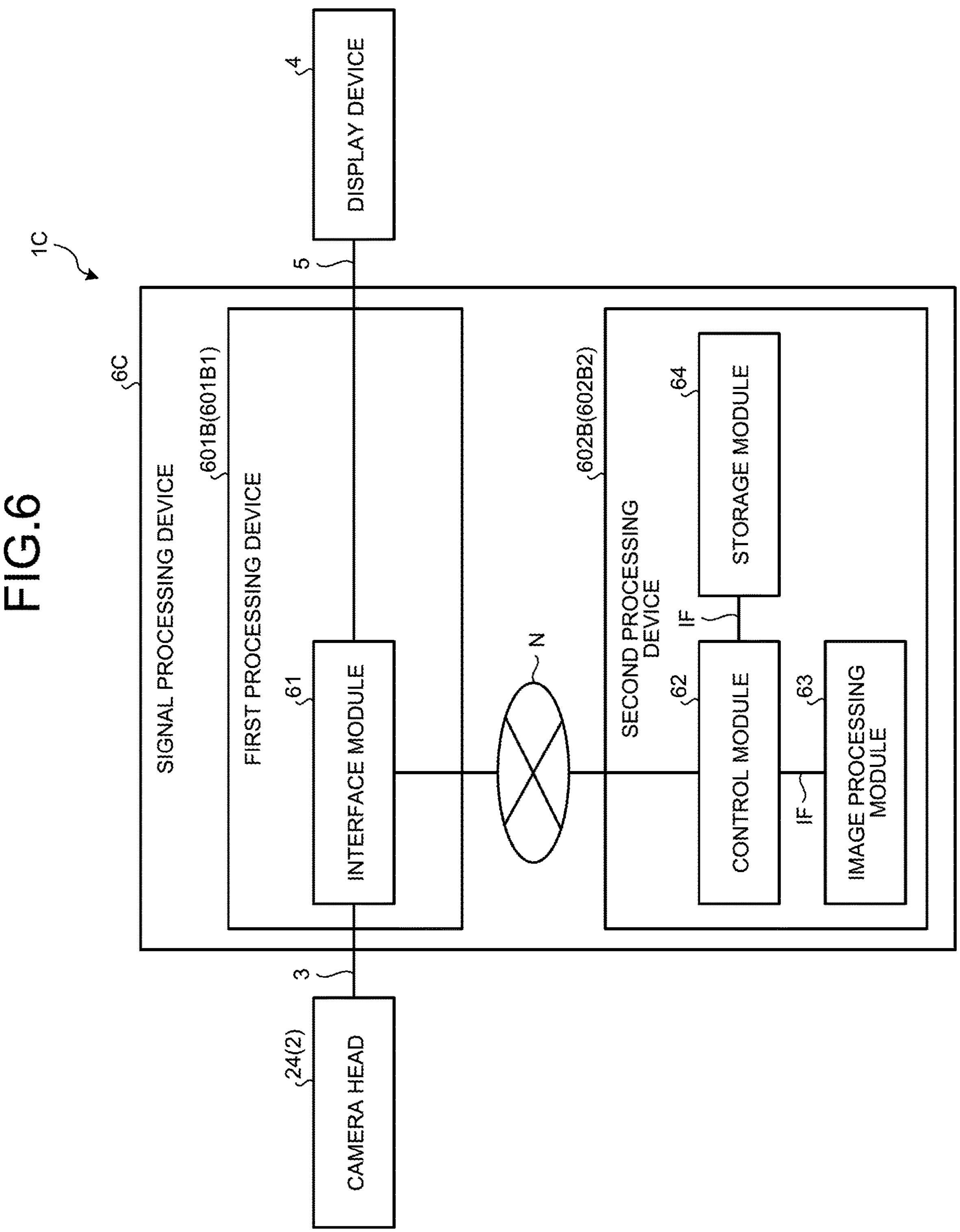
FIG. 6 is a diagram illustrating a general configuration of a signal processing device according to a fourth embodiment of the present invention.

FIG. 6 is a diagram illustrating a general configuration of a signal processing device 6C according to the fourth embodiment of the present invention.

The signal processing device 6C constituting a medical observation system 1C according to the fourth embodiment differs from the signal processing device 6B (FIG. 5) described in the third embodiment above only in that the first processing device 601B (interface module 61) and the second processing device 602B (control module 62) are connected via a network N such as the Internet.

According to the fourth embodiment described above, the following effects can be obtained in addition to the same effects as those described in the third embodiment above.

The configuration of the signal processing device 6C according to the fourth embodiment allows the second processing device 602B to include, for example, a dedicated server such as a cloud server. With this configuration, a higher-performance computer can be used for the second processing device 602B. For example, the processing performed by the internal modules 62 to 64 can be distributed. When other medical examinations using, for example, computerized tomography (CT), magnetic resonance imaging (MRI), and ultrasonic waves are previously performed on the same subject, a captured image captured by the endoscope 2 and examination images obtained from these examinations can be displayed on the display device 4 side by side or as a superimposed image.

Other Embodiments

Although some embodiments of the present invention have been described, these embodiments are not intended to limit the scope of the present invention.

In the first, third, and fourth embodiments above, the endoscope 2 (rigid endoscope) with a rigid scope (insert 21) is used as the medical observation apparatus according to the present invention, but the medical observation apparatus is not limited to this. For example, a flexible endoscope with a flexible scope (not illustrated) having an imaging device at the leading end of an insert may be used. The medical observation apparatus according to the present invention is not limited to the rigid endoscope or the flexible endoscope, but, for example, an ultrasonic endoscope having an ultrasonic probe at the leading end of an insert for examining the subject using ultrasonic waves may be employed.

In the first to fourth embodiments described above, for example, PCIe interfaces are employed as the interfaces IF, but the interface IF is not limited to this PCIe interface. Any interface may be employed as long as it conforms to a communication interface standard (e.g., PC/AT-compatibles standard), such as universal serial bus (USE), Ethernet (registered trademark), SATA, HDMI (registered trademark), IEEE 1394 (registered trademark), DisplayPort (registered trademark), RS232C, general purpose input/output (GPIO), or other generally used standard.

In the first to fourth embodiments described above, the camera head 24 is configured to output an imaging signal in the form of an optical signal, but is not limited to this. The camera head 24 may be configured to output the imaging signal in the form of an electric signal. In this case, the interface module 61 does not need to have a function of photoelectrically converting the imaging signal (optical signal) into an electric signal.

REFERENCE SIGNS LIST

1, 1A to 1C Medical observation system
2 Endoscope
3 First transmission cable
4, 4A Display device
5 Second transmission cable
6, 6A to 6C Signal processing device
7 Third transmission cable
8 Fourth transmission cable
21 Insert
22 Light source
23 Light guide
24, 24A Camera head
60 Outer housing
61 Interface module (first interface module)
61A Second interface module
62 Control module
63 Image processing module (first image processing module)
63A Second image processing module
64 Storage module
65 Third interface module
601B First processing device
601B1 First outer housing
602B Second processing device
602B2 Second outer housing
IF Interface
N Network

The invention claimed is:

1. A signal processing device connected to a medical observation apparatus that outputs a first signal, the signal processing device comprising:

processing circuitry;

a converter, implemented by the processing circuitry, that receives the first signal at a dedicated interface for the medical observation apparatus and converts the received first signal, wherein a communication protocol of the received first signal is dedicated to the medical observation apparatus and does not conform to a communication interface standard, into a second signal conforming to a communication protocol of the communication interface standard;

an interface, implemented by the processing circuitry, that connects to the converter and transmits the second signal; and an image processor, implemented by the processing circuitry, that connects to the interface, and processes the transmitted second signal, wherein on condition that a failure occurs in the image processor, the converter performs image processing instead of the image processor.

2. The signal processing device according to claim 1, wherein the converter further receives, as the first signal, an image signal, and the image processor performs image processing.

3. The signal processing device according to claim 2, wherein the signal processing device further comprises a storage, implemented by the processing circuitry, that stores a computer program that causes the image processor to perform the image processing.

4. The signal processing device according to claim 1, wherein the image processor further performs image processing by software processing, and the converter further generates the second signal via a hardware configuration.

5. The signal processing device according to claim 1, wherein the signal processing device further comprises:

a first outer housing that stores the converter, and a second outer housing, separate from the first outer housing, that stores the image processor.

6. The signal processing device according to claim 1, wherein the processing circuitry includes a plurality of CPUs.

7. The signal processing device according to claim 1, wherein:

a first signal has a first frame identification;

the image processor outputs a first video signal having a second frame identification based on the transmitted second signal to the converter; and the converter is further configured to determine whether the first frame identification and the second frame identification are the same or sequential, and, on condition that they are not, to output a second video signal based on a stored signal and otherwise to output the first video signal.

8. A medical observation system, comprising:

a medical observation apparatus that outputs a first signal having a communication protocol that is dedicated to the medical observation apparatus and does not conform to a communication interface standard; and a signal processing device connected to the medical observation apparatus, the signal processing device including processing circuitry, a converter, implemented by the processing circuitry, that receives the first signal at a dedicated interface for the medical observation apparatus and converts the received first signal into a second signal conforming to a communication protocol of the communication interface standard;

an interface, implemented by the processing circuitry, connected to the converter and transmits the second signal; and an image processor, implemented by the processing circuitry, that connects to the interface, and processes the transmitted second signal, wherein on condition that a failure occurs in the image processor, the converter performs image processing instead of the image processor.

9. The medical observation system according to claim 8, wherein the converter further receives, as the first signal, an image signal, and the image processor further performs image processing.

10. The medical observation system according to claim wherein the signal processing device further comprises a storage, implemented by the processing circuitry, that stores therein a computer program for causing the image processor to perform the image processing.

11. The medical observation system according to claim 9, wherein the image processor further performs image processing by software processing, and the converter generates the second signal via a hardware configuration.

12. The medical observation system according to claim 8, wherein the signal processing device further comprises a first outer housing that stores the converter, and a second outer housing, separate from the first outer housing, that stores the image processor.

13. The medical observation system according to claim 8, wherein the medical observation apparatus includes an imaging unit that captures an image of a subject and outputs, as the first signal, an imaging signal obtained by the imaging unit.

14. The medical observation system according to claim 8, wherein the processing circuitry includes a plurality of CPUs.

15. The medical observation system according to claim 8, wherein:

a first signal has a first frame identification;

the image processor outputs a first video signal having a second frame identification based on the transmitted second signal to the converter; and the converter is further configured to determine whether the first frame identification and the second frame identification are the same or sequential, and, on condition that they are not, to output a second video signal based on a stored signal and otherwise to output the first video signal.

16. A signal processing device connected to a medical observation apparatus that outputs a first signal and includes processing circuitry, the signal processing device comprising:

a converter, implemented by the processing circuitry, that receives the first signal and converts the received first signal having a communication protocol that into a second signal conforming to a communication protocol of a communication interface standard;

an interface, implemented by the processing circuitry, connects to the converter and transmits the second signal;

an image processor, implemented by the processing circuitry, that connects to the interface and processes the transmitted second signal;

a first outer housing that stores the converter, and a second outer housing, separate from the first outer housing, that stores the image processor.

* * * * *